(12) United States Patent
Vaillant et al.

(10) Patent No.: US 7,079,620 B2
(45) Date of Patent: Jul. 18, 2006

(54) METHOD AND APPARATUS FOR DETERMINING A MAGNIFICATION FACTOR A RADIOGRAPHIC IMAGE

(75) Inventors: Regis Vaillant, Villebo sur Yvette (FR); Franciso Sureda, Chatenay Malabry (FR); Jean Lienard, Clamart (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 200 days.

(21) Appl. No.: 10/099,698

(22) Filed: Mar. 13, 2002

(65) Prior Publication Data

US 2002/0141540 A1   Oct. 3, 2002

(30) Foreign Application Priority Data

Mar. 28, 2001   (FR) .................................. 01 04160

(51) Int. Cl.
*A61B 6/02* (2006.01)
*G03C 9/00* (2006.01)

(52) U.S. Cl. .......................................... 378/41; 378/62
(58) Field of Classification Search .................. 378/62, 378/165, 98.12, 98.2, 41, 42, 207; 600/425, 600/427; 382/128, 132, 131, 285, 286, 291
See application file for complete search history.

(56) References Cited

U.S. PATENT DOCUMENTS

| | | | | |
|---|---|---|---|---|
| 2,728,525 A | | 12/1955 | Holt .............................. 235/61 |
| 4,481,656 A | * | 11/1984 | Janssen et al. ............... 378/196 |
| 5,233,639 A | * | 8/1993 | Marks .......................... 378/42 |
| 5,293,574 A | * | 3/1994 | Roehm et al. ............. 378/98.2 |
| 5,359,637 A | * | 10/1994 | Webber .......................... 378/2 |
| 5,394,457 A | | 2/1995 | Leibinger et al. ........... 378/162 |
| 5,822,391 A | | 10/1998 | Whiting et al. ............ 378/98.2 |
| 6,047,080 A | | 4/2000 | Shiuh-Yung et al. ....... 382/128 |
| 6,289,235 B1 | * | 9/2001 | Webber et al. .............. 600/426 |
| 6,549,606 B1 | | 4/2003 | Lienard et al. |
| 6,816,564 B1 | * | 11/2004 | Charles et al. .................. 378/5 |

OTHER PUBLICATIONS

Deriche et al, "Tracking line segments", Image and Vision Computing, vol. 8, No. 4, p. 261-271, Nov. 1990.
Ding et al "Quantification of 3-D Coronary Arterial Motion Using Clinical Biplanes Intranglograms", International Journal of Cardiac Imaging, No. 16 pp. 331-346, 2000.

* cited by examiner

*Primary Examiner*—Edward J. Glick
*Assistant Examiner*—Thomas R. Artman
(74) *Attorney, Agent, or Firm*—Cantor Colburn LLP

(57) ABSTRACT

A method and apparatus for determining a magnification factor in a radiography device of the type comprising an X-ray source and means for acquiring images placed facing the source, the source and the means for acquiring images being mounted so as to rotate about at least one axis with respect to a support on which an object to be X-rayed is intended to be positioned. The method and the apparatus implementing the method comprises: acquiring at least two images corresponding to two different angular positions of the source and of the recording means with respect to the support; identifying on these images projections of at least one point of the X-rayed object; and determining the magnification factor of at least one of the images, first, as a function of the angular displacement of the source and of the recording means between the acquisitions of the images in question and, secondly, as a function of the positions on these images of the identified projections.

82 Claims, 1 Drawing Sheet

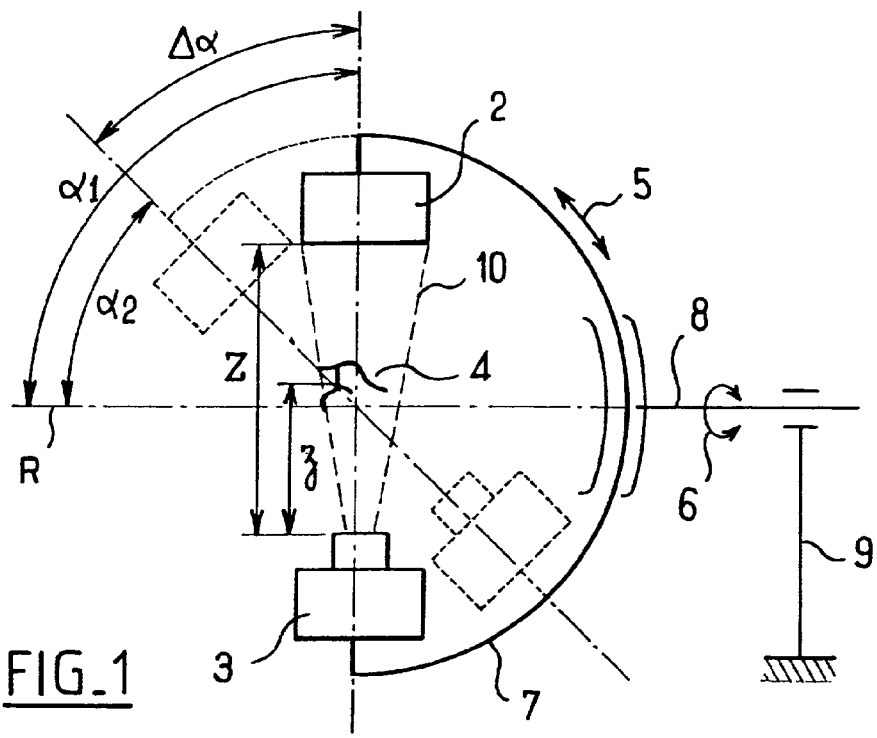
FIG_1
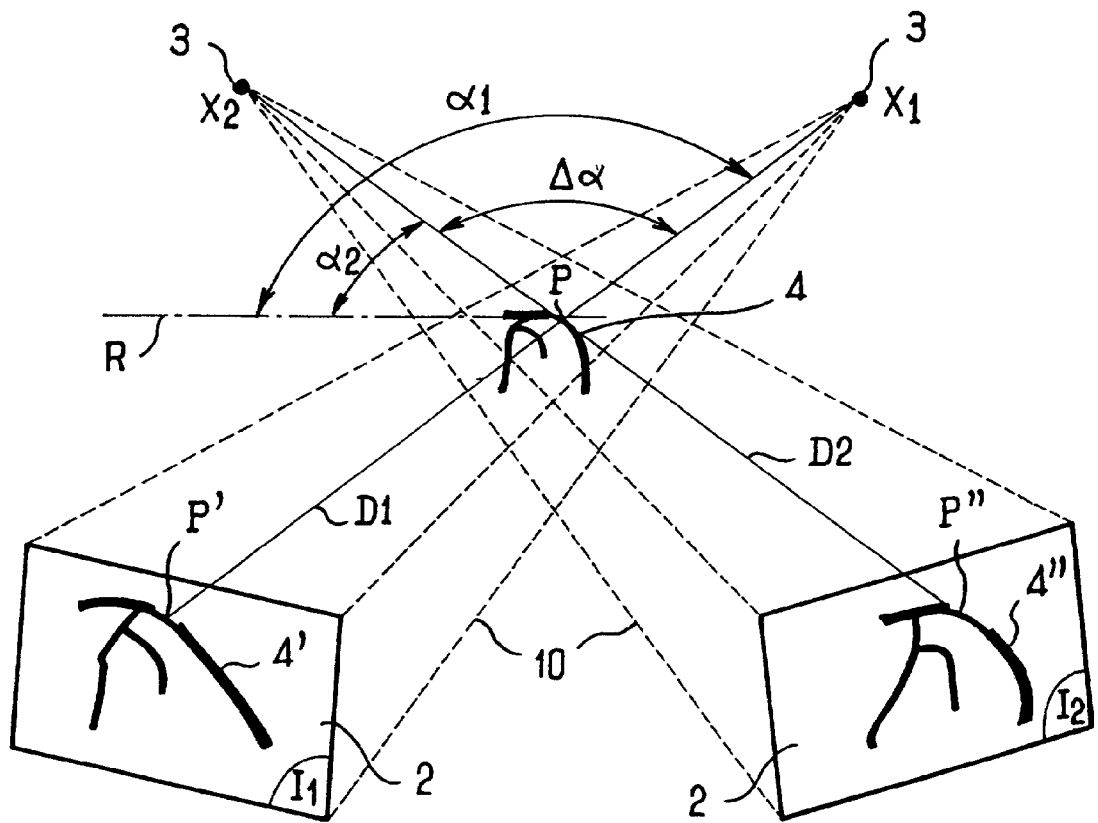
FIG_2

METHOD AND APPARATUS FOR DETERMINING A MAGNIFICATION FACTOR A RADIOGRAPHIC IMAGE

BACKGROUND OF THE INVENTION

This application claims the benefit of a priority under 35 USC 119 to French Patent Application No. 01 04 160 filed Mar. 28, 2001, the entire contents of which are incorporated by reference.

The invention relates to image acquisition methods by an X-ray radiography apparatus designed, in particular, for angiography.

In vascular imaging, in many cases, it is important to be able to identify the actual size of arteries from images from the X-ray radiography apparatus. This is because stenosis, a narrowing of the artery, is frequently treated by introducing a balloon into the artery and then by dilating the balloon to the size of the healthy artery. The size of the healthy artery is determined by measuring the artery on each side of the lesion due to the stenosis. This measurement is used to select a balloon of suitable size to treat the stenosis. The images from the x-ray radiographs are projections. Consequently, a magnification factor is determined to indicate the actual size of the artery from its size in the image. Several approaches have been proposed in order to calculate the magnification factor. One approach currently used is to locate a catheter (or any other object whose size is known) in the image and to determine its size in the image. The actual size of the object is entered into the apparatus. Thus, the magnification factor for the object is determined. Assuming that the distance to the projection center is similar for the object and for the artery, the same magnification factor is used to determine the size of the artery. This approach has several disadvantages. First, it requires the user to provide information which is not directly connected with the pathology, that is to say, the size of the instrument which is used as a calibration object. Should there be an error, a poor measurement is made. Second, the applied algorithm assumes that the calibration object and the artery to be measured are close to each other. This is almost never the case. Furthermore, in certain situations, when the user wishes to employ a catheter as a calibration object, the catheter is not necessarily visible on the image selected in order to measure the artery. This may lead to considerable errors of accuracy in determining the size of the artery, which is detrimental to the proper treatment of the stenosis.

BRIEF DESCRIPTION OF THE INVENTION

The present invention is to provide an embodiment of a method and an apparatus for determining the magnification factor. In an embodiment of the invention, a method of determining a magnification factor in a radiography apparatus of the type comprising means for providing an X-ray source and means for acquiring images, the source and the image acquisition being mounted so as to rotate about at least one axis with respect to an object to a support on which an object to be X-rayed is intended to be positioned, comprising acquiring at least two images corresponding to two different angular positions of the source and of the image acquisition with respect to the support; identifying on these images projections of at least one point of the X-rayed object; and determining the magnification factor of at least one of the images, first as a function of the angular displacement of the source and of the image acquisition between the acquisitions of the images in question and, secondly, as a function of the positions on these images of the identified projections.

Further, an embodiment of the invention is directed to an X-ray radiography apparatus, comprising means for providing an X-ray source and means for acquiring images, the source and the image acquisition being mounted so as to rotate about at least one axis with respect to a support on which an object to be X-rayed is intended to be positioned, the apparatus comprising means for processing the images acquired by implementing an embodiment of the method.

Also, in an embodiment of the invention, a method of acquiring vascular radiographic images by means of a radiography apparatus of the type comprising means for providing an X-ray source and means for acquiring images, the source and the image acquisition being mounted so as to rotate about at least one axis with respect to a support on which an object to be X-rayed is intended to be positioned, a method where a magnification factor is determined by implementing an embodiment of the method.

BRIEF DESCRIPTION OF THE DRAWINGS

The invention and embodiments thereof will become apparent from the following description and the appended drawings, in which:

FIG. 1 is a schematic view of a radiography device for implementing an embodiment of a method for determining a magnification fact or of a radiographic image; and FIG. 2 is an outline diagram showing the taking of two images from two different angles during an embodiment of the method.

DETAILED DESCRIPTION OF THE INVENTION

Referring to FIG. 1, an X-ray radiography apparatus 1 comprises means for taking a radiography image 2 and means for emitting X-rays 3 in the form of an X-ray source. The means for taking a radiographic images 2 is, for example, a digital camera. The X-ray source 3 and the camera 2 are attached to each end of an arm to form, in this example, a semicircle. The arm 7 is connected to a second arm 8 by, for example, sliding. The second arm 8 is itself connected, for example, by sliding and by rotating to a stand 9 of the radiography apparatus 1.

Arm 8 is capable of carrying out rotational movements 6 about its own axis. Arm 7, capable of sliding with respect to the arm 8, makes a rotational movement 5 with respect to the center of the semicircle forming arm 7.

In use, an object to be imaged, for example, the body of a patient, is positioned between the X-ray source 3 and the camera 2, so that an artery 4 to be X-rayed is in the imaging field 10 of the device. Artery 4 is then at a distance z from the X-ray source 3. By construction, the camera 2 is at a distance Z from this same X-ray source 3. The image of the artery 4 taken by the camera 2 is a projection whose magnification factor f is equal to the ratio Z/z.

In order to be able to calculate the magnification factor f, the X-ray radiography apparatus 1 determines the distance z, given that the distance Z is known because of construction of the apparatus. For this purpose, with reference to FIG. 2, the radiography apparatus takes a first image $I_1$ while the source 3 is in position $X_1$ in order to create an image at a first acquisition angle $\alpha_1$ with respect to a reference R. The artery 4 is identified on the image $I_1$ by its projection 4'. Next, the X-ray radiography apparatus 1 takes a second image $I_2$ at a second acquisition angle $\alpha_2$ with respect to the reference R, the X-ray source 3 then being in position $X_2$. Again, the artery 4 is identified on the image $I_2$, by its projection 4". Given the successive positions of the X-ray source 3 and $X_1$ and $X_2$, it is possible, by using triangulation calculation methods, to determine, on the basis of projections 4' and 4" of the artery 4, the spatial position of a point P of the artery 4 in the imaging field 10 of the radiography apparatus 1.

The triangulation comprises the determination of the coordinates of a point P belonging to the artery 4. For this purpose, the projection P' of the point P is identified on the image $I_1$. Given the coordinates for the position $X_1$ of the X-ray source 3, the equation of the straight line $D_1$ passing through $X_1$ and P' is determined. Similarly, the projection P" of the P is identified on the image $I_2$. Given the coordinates for the position $X_2$ of the X-ray source 3, the equation of the straight line $D_2$ passing through $X_2$ and P" is determined. The point P whose coordinates are sought is located in the middle of the segment of the common perpendicular of the straight lines $D_1$ and $D_2$, connecting the straight lines $D_1$ and $D_2$.

Given the spatial position of the point P of the artery 4, the radiography apparatus 1 can calculate the distance z separating the artery 4 from the X-ray source 3, for any one of the images taken. Hence, it thereby determines the magnification factor of this image in question and thereby deduces the actual size of the artery in question.

In order to displace the X-ray source from the position $X_1$ to the position $X_2$, the arm 7 rotates about the artery 4, either in the direction of rotation 6, or in the direction of rotation 5. The direction of rotation is chosen by the user according to the conditions of use of the radiography apparatus 1. During this rotation, the X-ray radiography apparatus takes a series of successive images in a burst at an acquisition rate varying, for example, from 15 images per second to 30 images per second. The series of images can be stored in a plurality of memories (not shown) of the radiography apparatus 1.

In order to carry out triangulation to determine the spatial position of the artery 4, the separation $\Delta\alpha$ between the angles $\alpha1$ and $\alpha_2$ is, for example, between 15° and 45°. Preferably, the separation $\Delta\alpha$ is equal to 20°. In order to rotate through an angle $\Delta\alpha$, the X-ray radiography apparatus 1 displaces the source 3 along one of the aforementioned directions of rotation 5, 6 at a rate of between, for example, 30° per second and 40° per second. For example, the radiography apparatus 1 is capable of taking a series of about 15 images for a separation $\Delta\alpha$ of 20°, at a speed of 40° per second, and for an image acquisition rate in a burst of 30 images per second. Over this series of images each one comprising a different projection of the artery 4, the radiography apparatus 1 will track the artery 4 by means of an image processing method which is implemented by a processor (not shown) of the radiography apparatus 1 which has access to the plurality of memories having stored the series of images. This image processing method enabling tracking of this kind can be carried out, for example, in two ways: First, either the apparatus determines a region around the artery 4 to be tracked and tracks this region throughout all the images constituting the series of images by optimizing a similarity criterion such as the correlation, or second the apparatus segments the artery over the first image and monitors this segmentation over the images constituting the series. Such tracking methods are described in the following publications: Zhaohua Ding & Morton H. Friedman "*Quantification of 3-D coronary arterial motion using clinical biplane cineangiograms*", the International Journal of Cardiac Imaging, No. 16, pages 331 to 346, 2000; and Deriche Rachid and Faugeras Olivier, "Tracking line segment", Image and vision computing, Volume 8, No. 4, pages 261 to 271, November 1990.

The X-ray radiography apparatus 1 implementing the method of acquiring and monitoring an artery is designed to be used mainly during surgical procedures within an operating theater. The user positions the radiography apparatus 1 around the object to image for example, a patient, so that the artery 4 which is desired to be studied is in the image field 10 of the radiography apparatus 1. Since the camera 2 and the X-ray source 3 are aligned at an angle $\alpha_1$ with respect to the reference R, the user takes a first image which will indicate to the radiography apparatus the artery 4 which is to be studied. Next the radiography apparatus 1 rotates the camera 2 and the X-ray source 3, which are in alignment, to an angle $\alpha_2$ with respect to the reference R. During this rotation through an angle $\Delta\alpha$, the apparatus takes a series of images in a burst, as has been described above. Over this series of images, the apparatus tracks the designated artery 4, determines the spatial position of the artery 4 in the imaging field 10 of the radiography apparatus 1 by means of triangulation. The magnification factor f is determined in order to be able to provide the user with the actual size of the artery 4 which is to be studied, from the size determined from the projection of the artery 4 on at least one of the acquired images. The apparatus will then be able to determine the exact shape of the artery in the form of variations of the cross section over a given segment, from the series of images.

Thus, it is no longer necessary for the user to enter the size of a known object. The position of the artery is determined in the imaging field of the radiography apparatus triangulation given the displacement angle and the position of the projections. Knowledge of this position makes it possible to determine the distance from the artery to the X-ray source. Knowing the distance form the image to the X-ray source of the radiography apparatus as a result of its construction, the magnification factor of this image can be accurately determined.

The embodiment of the apparatus and method has at least one of the following characteristics: at least two images on which an identification is carried out for the purpose of determining a magnification factor are acquired for angular positions separated by an angle greater than 15°; at least two images on which an identification is carried out for the purpose of determining a magnification factor are acquired for angular positions separated by an angle greater than 20°; during an image acquisition, a plurality of images is acquired between a first and a second angular position; identification of the projections implements automatic tracking of at least one point of the object from one image to another, on the plurality of images acquired; the automatic tracking implements monitoring by means of a similarity criterion of at least one region of the object; the similarity criterion is a correlation criterion; the automatic tracking implements monitoring of at least one segment that is identified on the images.

Various modifications in structure and/or steps and/or function may be made by one skilled in the art without departing form the scope and extent of the invention as recited in the claims.

What is claimed is:

1. A method of determining a magnification factor in a radiography apparatus comprising means for providing an X-ray source and means for acquiring images, the means for providing an X-ray source and the means for acquiring images being mounted so as to rotate about at least one axis with respect to a support on which an object to be X-rayed is intended to be positioned, comprising:

acquiring at least two images corresponding to two different angular positions separated by an angle greater than 15° of the means for providing an X-ray source and of the means for acquiring images with respect to the support;

identifying on these images projections of at least one point of the X-rayed object; the identification of the projections implements automatic tracking of at least one point of the object from one image to another, on the plurality of images acquired; and determining the magnification factor of at least one of the images, first, as a function of the angular displacement of the means for providing an X-ray source and of the means for acquiring images between the acquisitions of the images in question and, secondly, as a function of the positions on these images of the identified projections.

2. The method according to claim 1 wherein at least two images on which an identification is carried out for the purpose of determining a magnification factor are acquired for angular positions separated by an angle greater than 20°.

3. The method according to claim 2 wherein during an acquisition step, a plurality of images is acquired between a first and a second angular position.

4. The method according to claim 1 wherein the angle is greater than 20°.

5. The method according to claim 4 wherein during an acquisition step, a plurality of images is acquired between a first and a second angular position.

6. The method according to claim 1 wherein during an acquisition step, a plurality of images is acquired between a first and a second angular position.

7. The method according to claim 6 wherein automatic tracking implements monitoring of at least one segment that is identified on the images.

8. The method according to claim 1 wherein the automatic tracking implements monitoring by means of a similarity criterion of at least one region of the object.

9. The method according to claim 8 wherein the similarity criterion is a correlation criterion.

10. The method according to claim 1 wherein the angular positions are separated by an angle of between 15° and 45°.

11. An X-ray radiography apparatus comprising:

means for providing an X-ray source;

means for acquiring images;

the means for providing an X-ray source and the means for acquiring images being mounted so as to rotate about at least one axis with respect to a support on which an object to be X-rayed is intended to be positioned;

means for acquiring at least two images corresponding to two different angular positions separated by an angle greater than 15° of the means for providing an X-ray source and of the means for acquiring images with respect to the support;

means for identifying on these images projections of at least one point of the X-rayed object;

means for identification of the projections implementing automatic tracking of at least one point of the object from one image to another, on the plurality of images acquired; and means for determining the magnification factor of at least one of the images, first, as a function of the angular displacement of the means for providing an X-ray source and of the means for acquiring images between the acquisitions of the images in question and, secondly, as a function of the positions on these images of the identified projections.

12. The X-ray radiography apparatus according to claim 11 wherein at least two images on which an identification is carried out for the purpose of determining a magnification factor are acquired for angular positions separated by an angle greater than 20°.

13. The X-ray radiography apparatus according to claim 11 wherein the angle is greater than 20°.

14. The method according to claim 11 wherein the angular positions are separated by an angle of between 15° and 45°.

15. A method of determining a magnification factor of an object in a radiographic image comprising:

providing an X-ray source;

providing a means for acquiring images;

determining a distance from the means for acquiring images to the object;

providing a first projection of the object by taking a first image of the object while the X-ray source is in a first position in order to create the first image as a first angle with respect to a reference;

providing a second projection of the object by taking a second image of the object while the X-ray source is a second position in order to create the second image as a second angle with respect to the reference;

calculating on the basis of the projections a spatial position of a point in the object;

identification of the projections implements automatic tracking of at least one point of the object from one image to another, on the plurality of images acquired; and calculating the distance from the X-ray source to the object based on the spatial position to determine the magnification factor.

16. The method of claim 15 wherein the magnification factor is determined:

first, as a function of the angular displacement of the X-ray source and the means for acquiring images between the acquisitions of the images; and secondly, as a function of the position on these images of the first and second projections.

17. The method of claim 16 comprising:

taking a series of 15 images for the angular separation of 20° at a rotational speed of 40° per second; and for an image acquisition rate in a burst of 30 images per second.

18. The method of claim 15 wherein at least two images on which an identification is carried out for the purpose of determining a magnification factor are acquired for angular positions separated by an angle greater than 15°.

19. The method of claim 15 wherein at least two images on which an identification is carried out for the purpose of determining a magnification factor are acquired for angular positions separated by an angle greater than 20°.

20. The method of claim 15 wherein automatic tracking implements monitoring by means of a similarity criterion of at least one region of the object.

21. The method of claim 20 wherein the similarity criterion is a correlation criterion.

22. The method of claim 15 wherein automatic tracking implements monitoring of at least one segment that is identified on the images.

23. The method of claim 15 comprising taking a series of successive images in a burst as an acquisition rate varying from 15 images per second to 30 images per second.

24. The method of claim 15 wherein the first and second angles have an angular separation between 15° and 45°.

25. The method of claim 24 wherein the angular separation is 20°.

26. The method of claim 15 wherein the X-ray source and the means for acquiring images rotate about at least one axis relative to the reference as a rate of between 30° per second and 90° per second.

27. A method for acquiring vascular radiographic images by means of a radiography device comprising an X-ray source and means for acquiring images placed facing the source, the X-ray source and the means for acquiring images being mounted so as to rotate about at least one axis with respect to a support on which an object to be X-rayed is intended to be positioned, comprising determining a magnification factor by:
 acquiring at least two images corresponding to two different angular positions of the X-ray source and of the means for acquiring images with respect to the support;
 identifying on these images projections of at least one point of the X-rayed object; wherein the identification of the projections implements automatic tracking of at least one point of the object from one image to another, on the plurality of images acquired; and
 determining the magnification factor of at least one of the images, first, as a function of the angular displacement of the X-ray source and of the means for acquiring images between the acquisitions of the images in question and, secondly, as a function of the positions on these images of the identified projections.

28. The method according to claim 27 wherein at least two images on which an identification is carried out for the purpose of determining a magnification factor are acquired for angular positions separated by an angle greater than 15°.

29. The method according to claim 27 wherein at least two images on which an identification is carried out for the purpose of determining a magnification factor are acquired for angular positions separated by an angle greater than 20°.

30. The method according to claim 27 wherein the angular positions are separated by an angle of between 15° and 45°.

31. The method according to claim 27 wherein during an acquisition step, a plurality of images is acquired between a first and a second angular position.

32. The method according to claim 31 wherein the automatic tracking implements monitoring by means of a similarity criterion of at least one region of the object.

33. The method according to claim 32 wherein the similarity criterion is a correlation criterion.

34. The method according to claim 31 wherein automatic tracking implements monitoring of at least one segment that is identified on the images.

35. The method of claim 27 comprising taking a series of successive images in a burst as an acquisition rate varying from 15 images per second to 30 images per second.

36. The method of claim 27 wherein the X-ray source and the means for acquiring images rotate about at least one axis relative to the reference as a rate of between 30° per second and 90° per second.

37. The method of claim 27 wherein the angular separation is 20°.

38. The method of claim 33 comprising:
 taking a series of 15 images for the separation of 20° at a rotational speed of 40° per second; and
 for an image acquisition rate in a burst of 30 images per second.

39. A method of determining a magnification factor in a radiography apparatus comprising means for providing an X-ray source and means for acquiring images, the means for providing an X-ray source and the means for acquiring images being mounted so as to rotate about at least one axis with respect to a support on which an object to be X-rayed is intended to be positioned, comprising:
 acquiring at least two images corresponding to two different angular positions separated by an angle greater than 15° of the means for providing an X-ray source and of the means for acquiring images with respect to the support;
 identifying on these images projections of at least one point of the X-rayed object; and
 determining the magnification factor of at least one of the images, first, as a function of the angular displacement of the means for providing an X-ray source and of the means for acquiring images between the acquisitions of the images in question and, secondly, as a function of the positions on these images of the identified projections.

40. The method according to claim 39 wherein at least two images on which an identification is carried out for the purpose of determining a magnification factor are acquired for angular positions separated by an angle greater than 20°.

41. The method according to claim 40 wherein during an acquisition step, a plurality of images is acquired between a first and a second angular position.

42. The method according to claim 40 wherein the identification of the projections implements automatic tracking of at least one point of the object from one image to another, on the plurality of images acquired.

43. The method according to claim 39 wherein the angle is greater than 20°.

44. The method according to claim 43 wherein during an acquisition step, a plurality of images is acquired between a first and a second angular position.

45. The method according to claim 43 wherein the identification of the projections implements automatic tracking of at least one point of the object form one image to another, on the plurality of images acquired.

46. The method according to claim 39 wherein during an acquisition step, a plurality of images is acquired between a first and a second angular position.

47. The method according to claim 46 wherein the identification of the projections implements automatic tracking of at least one point of the object form one image to another, on the plurality of images acquired.

48. The method according to claim 46 wherein automatic tracking implements monitoring of at least one segment that is identified on the images.

49. The method according to claim 39 wherein the identification of the projections implements automatic tracking of at least one point of the object from one image to another, on the plurality of images acquired.

50. The method according to claim 49 wherein the automatic tracking implements monitoring by means of a similarity criterion of at least one region of the object.

51. The method according to claim 50 wherein the similarity criterion is a correlation criterion.

52. The method according to claim 39 wherein the angular positions are separated by an angle of between 15° and 45°.

53. An X-ray radiography apparatus comprising:
 means for providing an X-ray source;
 means for acquiring images;
 the means for providing an X-ray source and the means for acquiring images being mounted so as to rotate about at least one axis with respect to a support on which an object to be X-rayed is intended to be positioned;

means for acquiring at least two images corresponding to two different angular positions separated by an angle greater than 15° of the means for providing an X-ray source and of the means for acquiring images with respect to the support;

means for identifying on these images projections of at least one point of the X-rayed object; and means for determining the magnification factor of at least one of the images, first, as a function of the angular displacement of the means for providing an X-ray source and of the means for acquiring images between the acquisitions of the images in question and, secondly, as a function of the positions on these images of the identified projections.

54. The X-ray radiography apparatus according to claim 53 wherein at least two images on which an identification is carried out for the purpose of determining a magnification factor are acquired for angular positions separated by an angle greater than 20°.

55. The X-ray radiography apparatus according to claim 53 wherein the angle is greater than 20°.

56. The method according to claim 53 wherein the angular positions are separated by an angle of between 15° and 45°.

57. A method of determining a magnification factor of an object in a radiographic image comprising:

providing an X-ray source;
providing a means for acquiring images;
determining a distance from the means for acquiring images to the object;
providing a first projection of the object by taking a first image of the object while the X-ray source is in a first position in order to create the first image as a first angle with respect to a reference;
providing a second projection of the object by taking a second image of the object while the X-ray source is a second position in order to create the second image as a second angle with respect to the reference;
calculating on the basis of the projections a spatial position of a point in the object; and
calculating the distance from the X-ray source to the object based on the spatial position to determine the magnification factor.

58. The method of claim 57 wherein the magnification factor is determined:

first, as a function of the angular displacement of the X-ray source and the means for acquiring images between the acquisitions of the images; and
secondly, as a function of the position on these images of the first and second projections.

59. The method of claim 57 wherein at least two images on which an identification is carried out for the purpose of determining a magnification factor are acquired for angular positions separated by an angle greater than 15°.

60. The method of claim 57 wherein at least two images on which an identification is carried out for the purpose of determining a magnification factor are acquired for angular positions separated by an angle greater than 20°.

61. The method of claim 57 wherein the identification of the projections implements automatic tracking of at least one point of the object from one image to another, on the plurality of images acquired.

62. The method of claim 57 wherein automatic tracking implements monitoring by means of a similarity criterion of at least one region of the object.

63. The method of claim 62 wherein the similarity criterion is a correlation criterion.

64. The method of claim 57 wherein automatic tracking implements monitoring of at least one segment that is identified on the images.

65. The method of claim 57 comprising taking a series of successive images in a burst as an acquisition rate varying from 15 images per second to 30 images per second.

66. The method of claim 57 wherein the first and second angles have an angular separation between 15° and 45°.

67. The method of claim 66 wherein the angular separation is 20°.

68. The method of claim 57 wherein the X-ray source and the means for acquiring images rotate about at least one axis relative to the reference as a rate of between 30° per second and 90° per second.

69. The method of claim 57 comprising:

taking a series of 15 images for the angular separation of 20° at a rotational speed of 40° per second; and
for an image acquisition rate in a burst of 30 images per second.

70. A method for acquiring vascular radiographic images by means of a radiography device comprising an X-ray source and means for acquiring images placed facing the source, the X-ray source and the means for acquiring images being mounted so as to rotate about at least one axis with respect to a support on which an object to be X-rayed is intended to be positioned, comprising determining a magnification factor by:

acquiring at least two images corresponding to two different angular positions of the X-ray source and of the means for acquiring images with respect to the support;
identifying on these images projections of at least one point of the X-rayed object; and
determining the magnification factor of at least one of the images, first, as a function of the angular displacement of the X-ray source and of the means for acquiring images between the acquisitions of the images in question and, secondly, as a function of the positions on these images of the identified projections.

71. The method according to claim 70 wherein at least two images on which an identification is carried out for the purpose of determining a magnification factor are acquired for angular positions separated by an angle greater than 15°.

72. The method according to claim 70 wherein at least two images on which an identification is carried out for the purpose of determining a magnification factor are acquired for angular positions separated by an angle greater than 20°.

73. The method according to claim 70 wherein the angular positions are separated by an angle of between 15° and 45°.

74. The method according to claim 70 wherein during an acquisition step, a plurality of images is acquired between a first and a second angular position.

75. The method according to claim 74 wherein automatic tracking implements monitoring by means of a similarity criterion of at least one region of the object.

76. The method according to claim 75 wherein the similarity criterion is a correlation criterion.

77. The method according to claim 74 wherein automatic tracking implements monitoring of at least one segment that is identified on the images.

78. The method according to claim 70 wherein the identification of the projections implements automatic tracking of at least one point of the object from one image to another, on the plurality of images acquired.

79. The method of claim 70 comprising taking a series of successive images in a burst as an acquisition rate varying from 15 images per second to 30 images per second.

80. The method of claim 70 wherein the X-ray source and the means for acquiring images rotate about at least one axis relative to the reference as a rate of between 30° per second and 90° per second.

81. The method of claim 70 wherein the angular separation is 20°.

82. The method of claim 70 comprising:
taking a series of 15 images for the separation of 20° at a rotational speed of 40° per second; and
for an image acquisition rate in a burst of 30 images per second.

* * * * *

UNITED STATES PATENT AND TRADEMARK OFFICE
CERTIFICATE OF CORRECTION

PATENT NO.         : 7,079,620 B2                                   Page 1 of 1
APPLICATION NO.    : 10/099698
DATED              : July 18, 2006
INVENTOR(S)        : Vaillant et al.

It is certified that error appears in the above-identified patent and that said Letters Patent is hereby corrected as shown below:

<u>Title Page:</u>
Item (54), line 3 after "FACTOR" insert --OF--

<u>Column 1:</u>
Line 3, after "FACTOR" insert --OF--

<u>Column 8:</u>
Line 46, after "object" delete "form" and insert --from--

Signed and Sealed this

Ninth Day of January, 2007

JON W. DUDAS
*Director of the United States Patent and Trademark Office*